US012137888B2

(12) United States Patent
Smith et al.

(10) Patent No.: US 12,137,888 B2
(45) Date of Patent: Nov. 12, 2024

(54) FASTENING DEVICE AND RELATED METHODS OF USE

(71) Applicant: Boston Scientific Scimed, Inc., Maple Grove, MN (US)

(72) Inventors: Paul Smith, Smithfield, RI (US); Jeffrey Bean, Fitchburg, MA (US); John Golden, Norton, MA (US); Kenneth Keene, Winchester, MA (US); Douglas Melanson, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1051 days.

(21) Appl. No.: 16/936,862

(22) Filed: Jul. 23, 2020

(65) Prior Publication Data

US 2021/0022720 A1 Jan. 28, 2021

Related U.S. Application Data

(60) Provisional application No. 62/877,958, filed on Jul. 24, 2019.

(51) Int. Cl.
*A61B 17/00* (2006.01)
*A61B 1/00* (2006.01)
*A61B 17/072* (2006.01)

(52) U.S. Cl.
CPC .... *A61B 17/00234* (2013.01); *A61B 1/00133* (2013.01); *A61B 1/0014* (2013.01); *A61B 17/072* (2013.01); *A61B 2017/00296* (2013.01); *A61B 2017/00398* (2013.01); *A61B 2017/00473* (2013.01); *A61B 2017/00862* (2013.01); *A61B 2017/07257* (2013.01)

(58) Field of Classification Search
CPC .......... A61B 17/00234; A61B 1/00133; A61B 1/0014; A61B 17/072; A61B 2017/00296; A61B 2017/00398; A61B 2017/00473; A61B 2017/00862; A61B 2017/07257; A61B 1/00101; A61B 2017/07214
See application file for complete search history.

(56) References Cited

U.S. PATENT DOCUMENTS 4,671,445 A * 6/1987 Barker ................. A61B 17/115 227/19
4,763,662 A * 8/1988 Yokoi ................ A61B 1/00098 600/101
5,326,013 A * 7/1994 Green ............. A61B 17/07207 227/176.1
5,364,001 A * 11/1994 Bryan ............. A61B 17/07207 227/19

(Continued)

FOREIGN PATENT DOCUMENTS

EP 2456364 B1 5/2012
JP 2000-166936 A 6/2000

(Continued)

*Primary Examiner* — Anh Tuan T Nguyen
*Assistant Examiner* — Shankar Raj Ghimire
(74) *Attorney, Agent, or Firm* — Bookoff McAndrews, PLLC

(57) ABSTRACT

A fastening mechanism that comprises an actuator, a fastening device attached to a distal end of the actuator, and a device coupler, wherein the fastening device is pivotally attached to the device coupler.

20 Claims, 3 Drawing Sheets

200 108a 109 108 106 108c 110 112 112a 108b 112c 108d 112b 100 116 102 123 124 104 122 124 114 120 126 118

10 106 108a 109 100 102 123 108b 116 30 104 108 110 118 124 126 120 122 114

(56) References Cited

U.S. PATENT DOCUMENTS 5,376,095 A * 12/1994 Ortiz .................. A61B 17/0686 227/181.1
5,381,943 A * 1/1995 Allen ................. A61B 17/0682 227/19
5,484,095 A * 1/1996 Green ................ A61B 17/0686 227/181.1
5,560,532 A * 10/1996 DeFonzo ........... A61B 17/0684 227/176.1
5,607,095 A * 3/1997 Smith ................ A61B 17/0682 227/176.1
5,916,146 A * 6/1999 Allotta ................... A61B 34/71 600/141
6,119,913 A * 9/2000 Adams ................. A61B 17/115 227/176.1
6,126,058 A * 10/2000 Adams ............. A61B 17/07207 227/19
6,241,140 B1 * 6/2001 Adams ............. A61B 17/07207 227/176.1
6,820,791 B2 * 11/2004 Adams ................ A61B 17/1114 227/180.1
7,575,548 B2 * 8/2009 Takemoto .............. A61B 1/018 600/122
8,033,442 B2 * 10/2011 Racenet ............... A61B 17/068 227/181.1
8,043,207 B2 * 10/2011 Adams ................ A61B 17/1114 600/128
8,096,459 B2 * 1/2012 Ortiz .................... A61B 17/072 227/176.1
8,663,241 B2 * 3/2014 Adams ............. A61B 17/07207 606/220
9,050,084 B2 * 6/2015 Schmid ............ A61B 17/07292
9,055,941 B2 * 6/2015 Schmid .............. A61B 17/0643
9,254,132 B2 * 2/2016 Crews .................. A61B 17/115
2002/0020732 A1 * 2/2002 Adams ................. A61B 17/072 227/19
2002/0047036 A1 * 4/2002 Sullivan ........... A61B 17/07207 227/19
2002/0063143 A1 * 5/2002 Adams ............... A61B 1/00087 227/180.1
2004/0059346 A1 * 3/2004 Adams ............. A61B 17/07207 606/115
2004/0084505 A1 * 5/2004 Bilotti .................. A61B 17/115 227/19
2004/0134964 A1 * 7/2004 Adams ................. A61B 17/072 227/176.1
2005/0065398 A1 * 3/2005 Adams ................ A61B 17/1114 600/128
2005/0234297 A1 * 10/2005 Devierre ............ A61B 1/00087 600/129
2006/0011699 A1 * 1/2006 Olson .............. A61B 17/07207 227/19
2006/0190029 A1 * 8/2006 Wales .............. A61B 17/00234 606/205
2006/0190032 A1 * 8/2006 Wales .............. A61B 17/00234 606/205
2007/0039997 A1 * 2/2007 Mather ................ A61B 17/072 227/176.1
2007/0114261 A1 * 5/2007 Ortiz ................ A61B 17/07207 227/175.1
2008/0177135 A1 * 7/2008 Muyari ............. A61B 1/00087 600/104
2008/0249354 A1 * 10/2008 Muyari ............. A61B 18/1492 600/104
2008/0265001 A1 * 10/2008 Green .............. A61B 17/07207 227/180.1
2008/0308607 A1 * 12/2008 Timm .............. A61B 17/07207 227/176.1
2009/0236399 A1 * 9/2009 Bilotti .................. A61B 17/072 227/176.1
2009/0236401 A1 * 9/2009 Cole .................... A61B 17/072 227/176.1
2010/0038403 A1 * 2/2010 D'Arcangelo ....... A61B 17/072 227/176.1
2010/0320252 A1 * 12/2010 Viola ................... A61B 17/068 227/176.1
2012/0232339 A1 * 9/2012 Csiky ................. A61B 1/00128 604/95.04
2013/0053644 A1 * 2/2013 Smith ................ A61B 1/00142 604/528
2013/0284792 A1 * 10/2013 Ma ..................... A61B 17/1155 227/176.1
2014/0008413 A1 * 1/2014 Williams ........... A61B 17/1155 227/179.1
2015/0150620 A1 * 6/2015 Miyamoto ......... A61B 18/1445 227/176.1
2015/0305742 A1 * 10/2015 Williams ........... A61B 17/1155 227/177.1
2016/0029875 A1 * 2/2016 Okada ................ A61B 1/00101 600/107
2016/0262744 A1 * 9/2016 Milo .................... A61B 17/105
2017/0333044 A1 * 11/2017 Sgroi, Jr. ........... A61B 17/1155
2019/0046180 A1 * 2/2019 Williams ........... A61B 17/1152
2019/0069887 A1 * 3/2019 Satti, III ................ A61B 17/29
2019/0167267 A1 * 6/2019 Kobayashi ....... A61B 17/07207
2019/0298373 A1 * 10/2019 Guerrera ............ A61B 17/1155
2020/0046353 A1 * 2/2020 Deck ................ A61B 17/07207
2020/0205817 A1 * 7/2020 Nielsen .............. A61B 17/1155
2020/0275925 A1 * 9/2020 Smith ................ A61B 1/00137
2021/0007736 A1 * 1/2021 Smith .............. A61B 17/00234
2021/0022720 A1 * 1/2021 Smith .............. A61B 17/00234
2022/0015767 A1 * 1/2022 Williams ........... A61B 17/1155
2022/0202417 A1 * 6/2022 Wenchell, Jr. ......... A61B 34/30
2023/0134917 A1 * 5/2023 Amanov ................ A61B 1/015 606/148

FOREIGN PATENT DOCUMENTS

WO 2014199759 A1 12/2014
WO 2020180678 A1 9/2020

* cited by examiner

FASTENING DEVICE AND RELATED METHODS OF USE

CROSS-REFERENCE TO RELATED APPLICATIONS

This application claims the benefit of priority from U.S. Provisional Application No. 62/877,958, filed Jul. 24, 2019, which is incorporated by reference herein in its entirety.

TECHNICAL FIELD

The present disclosure relates generally to tissue stapling. More particularly, at least some embodiments of the present disclosure relate to a fastening mechanism for a medical device, for example an endoscopic stapler, and related methods of using the fastening mechanism.

BACKGROUND

Stapling is used in many medical procedures, including laparoscopic procedures for example. These procedures often involve resecting portions or sections of tissue, followed by closing using staples. An exemplary procedure is colorectal anastomosis. In hybrid surgeries where physicians use laparoscopic and endoscopic platforms to conduct a procedure, a rigid stapler is often used. Linear staplers, which may include long rigid members, may be incapable of being navigated through tortuous anatomy without causing trauma to the tissue.

SUMMARY OF THE DISCLOSURE

According to an example, a fastening mechanism includes an actuator, a fastening device attached to a distal end of the actuator, and a device coupler. The fastening device is pivotally attached to the device coupler.

In another example, the actuator may move longitudinally to pivot the fastening device relative to the device coupler. The fastening mechanism may further include a sheath, wherein the sheath covers a portion of the actuator, and the actuator is longitudinally movable relative to the sheath. The actuator may include at least one inner drive mechanism that actuates the fastening device to open and close the fastening device and/or deploy fasteners. The fastening device may be a stapler that includes a head and an anvil, and the head includes a stapler cartridge from which staples are held and deployed. The stapler cartridge may include a plurality of longitudinal slots from which a plurality of staples are deployed. The head of the stapler may be comprised of a flexible material that allows the head to flex laterally. A proximal end of the actuator may be connected to a controller that operates the fastening mechanism. The controller may operate longitudinally moving the actuator in either direction, opening the fastening device, and/or simultaneously deploying fasteners and closing the fastening device. The actuator may be comprised of a flexible material. The device coupler may include a proximal support fixed to a distal support, wherein the proximal support is fixed to the sheath. The fastening device may be pivotally attached to the distal support of the device coupler. The proximal support may include at least one flexible arm. The distal support may define a lumen with an open distal end or a clear barrier at the end of the lumen.

According to an example, a fastening mechanism includes an actuator, a stapler attached to a distal end of the actuator, a sheath in which the actuator moves longitudinally, and a device coupler for attaching the stapler to an outer surface of a distal end of a medical device. The device coupler includes a proximal support and a distal support, the proximal support is fixedly coupled to the sheath, and the stapler is pivotally attached to the distal support of the device coupler.

In another example, the medical device may be an endoscope, and the proximal support and the distal support may be fixed to a distal end of the endoscope. The actuator may be longitudinally movable relative to the sheath to pivot the stapler relative to the device coupler. The actuator may include at least one inner drive mechanism that actuates the stapler to open and close the stapler and/or deploy staples.

According to an example, a method of fastening tissue includes inserting an endoscope and a stapling mechanism fixed to an external surface of the endoscope, into a natural orifice of a subject, delivering the endoscope and the stapling mechanism to target tissue, pivoting the stapling mechanism relative to the distal end of the endoscope, positioning tissue between a head and an anvil of the stapling mechanism, and deploying a staple from the stapler mechanism to fasten the target tissue.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Figure 1:
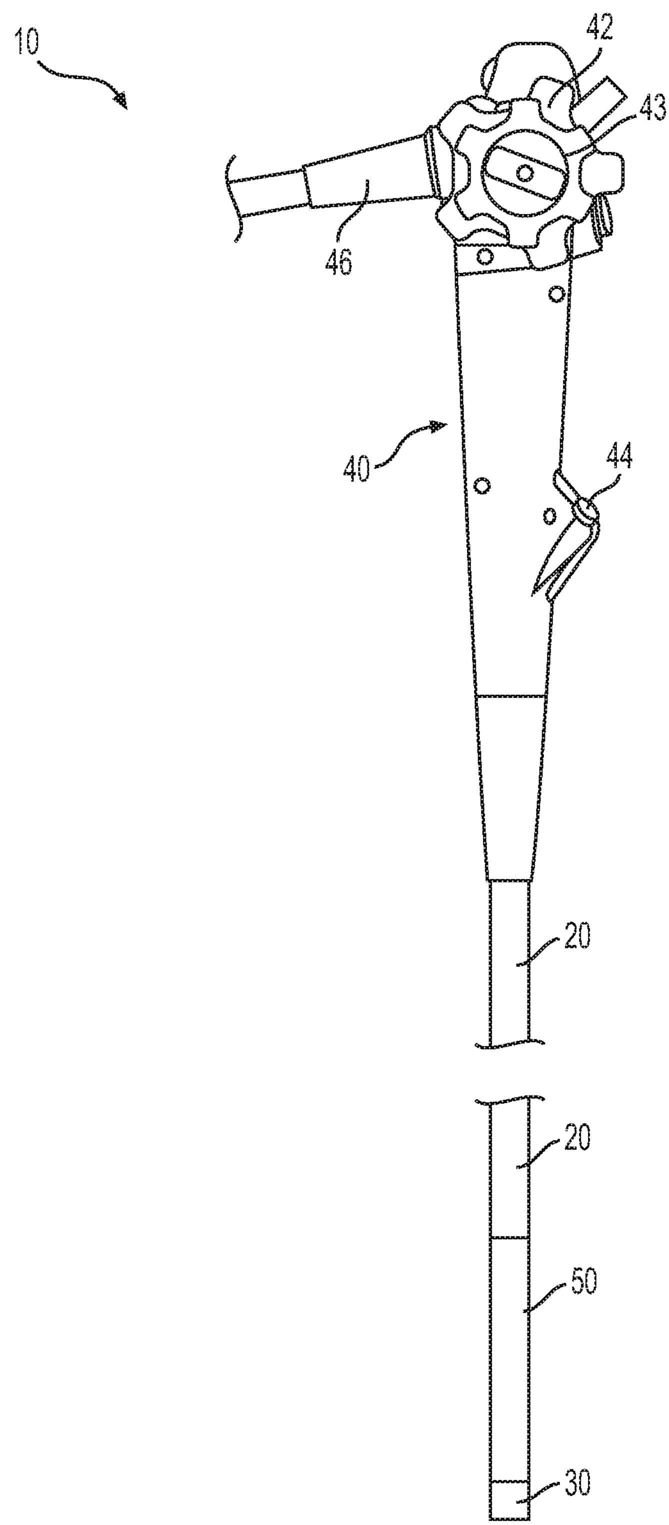
FIG. 1 is a perspective view of an endoscope according to an embodiment.

Endoscopic stapling may be especially useful in endoscopic, outpatient procedures. The present disclosure may solve one or more of the problems in the art. The scope of the disclosure, however, is defined by the attached claims and not the ability to solve a specific problem. The present disclosure is drawn to systems and devices, and related methods, for a stapling mechanism of a medical device, among other aspects. Referring to FIG. 1, an endoscope 10 according to an embodiment is shown. Endoscope 10 includes a flexible shaft 20, a tip 30 at a distal end of endoscope 10, and an articulation joint 50 disposed between and connecting flexible shaft 20 and tip 30. A handle 40 or some other device for actuating or controlling endoscope 10, and any tool or devices associated with endoscope 10, is connected at a proximal end of flexible shaft 20.

A plurality of actuating elements (not shown), such as cables or wires suitable for medical procedures (e.g., medical grade plastic or metal), may extend distally from a proximal end of endoscope 10 (such as handle 40) to articulation joint 50 and/or tip 30. For example, articulation/actuation wires may be indirectly coupled to first and second actuating devices 42, 43, which control articulation of articulation joint 50 in multiple directions, such as up, down, left, and right. Devices 42, 43, may be, for example, rotatable knobs that rotate about their axes to push/pull actuating elements.

Alternatively, or additionally, a user may operate actuating elements independently of handle 40. Distal ends of actuating elements extend through flexible shaft 20 and terminate at articulation joint 50 and/or tip 30. For example, one or more actuating elements may be connected to articulation joint 50 and one or more other actuating elements may be attached to tip 30. Actuation of actuating elements may control actuating joint 50, tip 30, and/or elements attached to tip 30, such as an end effector (not shown). In addition, one or more electrical cables (not shown) may extend from the proximal end of endoscope 10 (such as handle 40) to tip 30 and may provide electrical controls to imaging, lighting, and/or other electrical devices in or on tip 30, and may carry imaging signals from tip 30 proximally to be processed and/or displayed on a display. Handle 40 also may include a port 44 for introducing and/or removing tools, fluids, or other materials to and from the patient. A strain relief 46 attaches to an umbilicus for introducing fluid, suction, and/or wiring for electronic components. Endoscope 10 is an exemplary endoscope, in which a stapling mechanism may be attachable. The disclosure is not limited to a stapling mechanism for use in connection with endoscope 10. Any other medical scope (e.g. colonoscope, ureteroscope, duodenoscope, etc.), catheter, sheath, or the like, may be used in combination with the stapling mechanisms of this disclosure.

Figure 2:
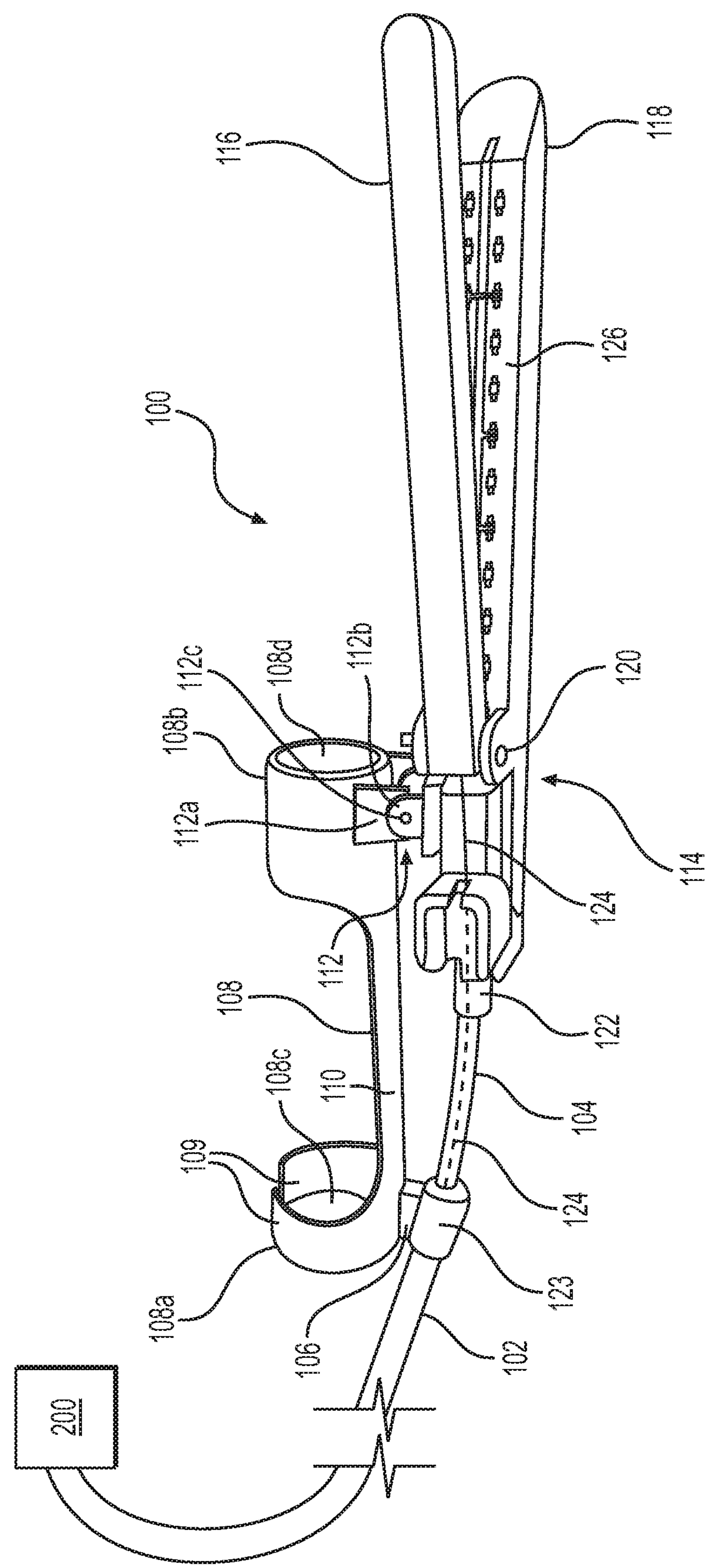
FIG. 2 is a perspective view of a stapling mechanism according to an embodiment.

Referring to FIG. 2, an embodiment of a stapling mechanism 100 for a medical device, including, but not limited to, an endoscope, e.g., endoscope 10, is shown. Stapling mechanism 100 includes an actuator 104, a sheath 102, a device coupler 108, and a stapler 114.

Actuator 104 is a flexible tube, made of plastic or other suitable biocompatible, flexible material. Actuator 104 is sufficiently long to extend along a complete length of an endoscope, such as the flexible shaft 20 of endoscope 10, and sufficiently flexible to traverse tortuous anatomy of a patient. The distal end of actuator 104 is attached to the proximal end of stapler 114 via a stapler connector 122. The proximal end of actuator 104, at least a portion of which is sheathed by sheath 102, may be connected to any suitable controller or handle known in the art, represented by the box 200, at the proximal end of stapling mechanism 100.

Sheath 102 also is a flexible tube, made of plastic or other suitable biocompatible, flexible material. Sheath 102, in embodiments, is sufficiently long to extend along a complete length of an endoscope, such as the flexible shaft 20 of endoscope 10, and sufficiently flexible to traverse tortuous anatomy of a patient. The distal end of sheath 102 is fixedly attached to a sheath connector 106 at coupler 123. The sheath 102 may be coaxial with the actuator 104. Like actuator 104, the proximal end of sheath 102 also may be connected to any suitable controller or handle known in the art, e.g., box 200, at the proximal end of stapling mechanism 100, in such a manner to permit longitudinal sliding of actuator 104 within sheath 102. The controller may actuate the stapling mechanism to perform operations including, but not limited to, longitudinally moving actuator 104 in either direction (distally or proximally) by extending or pulling on actuator 104 relative to sheath 102. The controller also may control a stapling operation of stapler 114, to staple intended target tissue.

With continued reference to FIG. 2, device coupler 108 has a proximal support 108*a*, a distal support 108*b*, and a coupler arm 110 connecting proximal support 108*a* and distal support 108*b*. Proximal support 108*a* includes sheath connector 106 and two arms 109 that can wrap around a medical device including, for example, an endoscope shaft or articulation joint. In some embodiments, the arms 109 may be flexible, e.g., to elastically deflect, or flex apart from each other. Arms 109 define an opening 108*c* that accepts the medical device. Each arm 109 may deflect, or flex radially outward to accept the medical device, and be biased radially inward to rigidly couple to the medical device, e.g., to engage circumferentially around the endoscope 10. In other embodiments, proximal support 108*a* may be in different configurations that may also hold and support a medical device, including, but not limited to, a single flexible arm or a single ring. Sheath connector 106 fixedly attaches proximal support 108*a* to sheath 102. This may ensure a more stable linkage between device coupler 108 and sheath 102.

As shown in FIG. 2, distal support 108*b* is an annular, cap-like, ring defining a lumen 108*d* therein. Support 108*b* may hold and support a distal end of a medical device including, but not limited to, an endoscope tip. Distal support 108*b* may have an open distal end. In other embodiments, distal support 108*b* may have a distal end having a transparent, clear cover or barrier, serving as a cap over the distal face of the medical device tip. An open distal end or a clear cap on its distal end allows endoscope 10 to continue its various functions, such as providing a source of light and imaging via its camera, without being impeded. In other embodiments, distal support 108*b* may be substituted with other various supports, embodying different configurations that may also hold and support a medical device.

Proximal support 108*a* is connected to distal support 108*b* via coupler arm 110. Coupler arm 110 is grooved, or curved, to accommodate the shape of a medical device resting upon coupler arm 110. Distal support 108*b* is attached to a proximal end of stapler 114 via a pivot connection 112. Pivot connection 112 includes a distal support linking arm 112*a*, stapler linking arms 112*b*, and a pivot pin 112*c* that pins distal support linking arm 112*a* and stapler linking arms 112*b* together. Distal support linking arm 112*a* is fixedly attached to and extends from distal support 108*b*, while stapler linking arms 112*b* are fixedly attached to and extend from a proximal location of stapler 114. Both distal support linking arm 112*a* and stapler linking arms 112*b* have a pin hole. In pivot connection 112, distal support linking arm 112*a* and stapler linking arms 112*b* overlap with one another, so that distal support linking arm 112*a* lies between the arms of stapler linking arms 112*b* and their respective pin holes align, thereby allowing pivot pin 112*c* to be inserted and pin them together. Pivot connection 112 allows for the rotation of stapler 114, about pivot pin 112*c* and relative to device coupler 108, by the longitudinal movement of actuator 104 relative to sheath 102. For example, actuator 104 may be extended distally by, for example, an operation of a controller, e.g., box 200, to which it is attached. In another example, actuator 104 may be pulled proximally relative to sheath 102, resulting in stapler 114 rotating or pivoting in an opposite direction about the longitudinal axis of pivot pin 112*c*.

Figure 3:
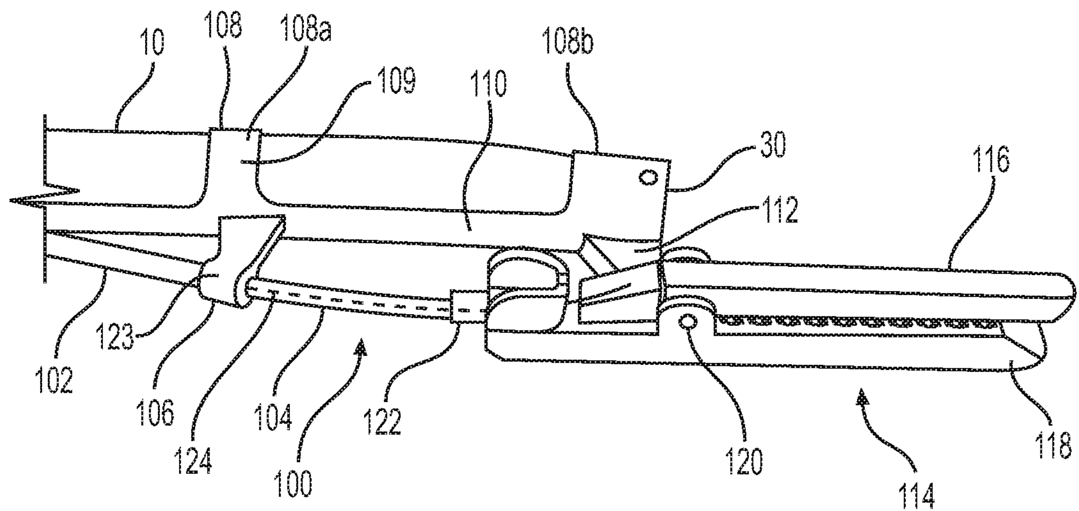
FIG. 3 is a perspective view of the stapling mechanism coupled to an endoscope, according to an embodiment.

Referring to FIG. 3, proximal support 108*a* is fixed, via two arms 109, relative to a distal location of endoscope 10, such as, at articulation joint 50 (referring to FIG. 1). As shown, arms 109 receive endoscope 10, thereby coupling endoscope 10 to stapling mechanism 100. Fixing stapling mechanism 100 relative to a distal location of endoscope 10 via proximal support 108*a* provides a base from which actuator 104 extends towards stapler 114 to rotate stapler 114 in a clockwise or counter-clockwise direction.

Figure 4:
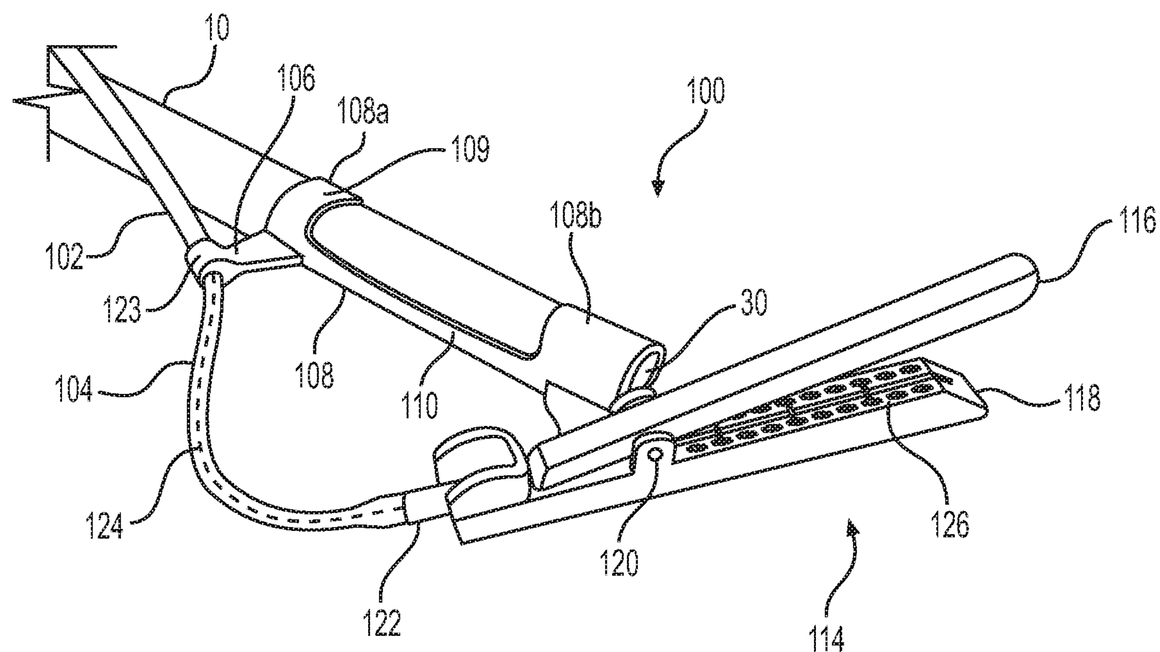
FIG. 4 is another perspective view of the stapling mechanism and endoscope of FIG. 3.

FIG. 4 is another perspective view of the embodiment shown in FIG. 3. As shown, actuator 104 is extended distally, thereby pivoting stapler 114 about pivot connection 112 in a counter-clockwise direction. As evident from FIG. 4, the degree by which stapler 114 may be rotated clockwise or counter-clockwise may be adjusted based on the degree by which actuator 104 is moved longitudinally in either direction. For example, the further actuator 104 is extended distally, the further stapler 114 will pivot about pivot connection 112 in a counter-clockwise direction, until the rotation of stapler 114 is impeded by the presence of device coupler 108. Likewise, the further actuator 104 is pulled proximally, the further stapler 114 will pivot about pivot connection 112 and rotate in a clockwise direction, until the rotation of stapler 114 is impeded by the presence of device coupler 108.

FIG. 4 also illustrates stapler 114 in an open position. In the open position, the distal ends of an anvil 116 and a head 118 of stapler 114 are spaced apart, thereby forming a gap in which materials including, but not limited to, tissue may be held within and stapled together. In a closed position, inner surfaces of anvil 116 and head 118 are in a closest position relative to each other, so that very little gap, or no gap, exists between the inner surfaces of anvil 116 and head 118, as illustrated in FIG. 3. Stapler 114 can be opened or closed by anvil 116 pivoting about a stapler pivot 120, which holds anvil 116 and head 118 together at a proximal location of stapler 114.

Actuation of a drive mechanism opens and closes stapler 114. With reference to FIG. 4, a wire 124 is within a lumen of actuator 104, and the distal end of wire 124 connects to a proximal end of anvil 116. The proximal end of wire 124 may connect to a controller (not shown) at the proximal end of stapling mechanism 100. When wire 124 is pulled proximally, anvil 116 may rotate about stapler pivot 120, to open stapler 114. Pushing wire 124 distally may rotate anvil 116 about stapler pivot, to close stapler 114.

FIG. 4 further illustrates that head 118 includes a stapler cartridge 126, from which one or more staples may be held and deployed. The mechanism of deploying staples may be actuated by another drive mechanism (not shown), e.g. a second inner drive mechanism, within the lumen of actuator 104. The form of this second inner drive mechanism is not particularly limited, and it may be in the form of another wire (not shown) within actuator 104. The distal end of this second inner wire may connect to a mechanism with head 118 that will deploy one or more staples. The proximal end of the second inner wire may connect to a controller (not shown), which may trigger the second inner wire to actuate the deployment of a staple from head 118, by operation thereof. Inner wire 124 and the second inner wire (for deployment of staples) may work in conjunction, by operation of a controller, to simultaneously deploy a staple and close the stapler, thereby securely stapling an intended target, e.g., tissue. In some embodiments, wire 124 that opens and closes stapler 114 and the second drive mechanism for deploying one or more staples, may be operated from the same controller. In other embodiments, the different drive mechanisms may be operated by different controllers.

In an embodiment, head 118 may contain a plurality of staples in stapler cartridge 126, which may be deployed from stapler cartridge 126 when under the influence of a driving force exerted by an actuation sled (not shown), as disclosed in U.S. Patent Application No. 62/812,538, "Systems, Device, and Related Methods for Fastening Tissue", filed Mar. 1, 2019, the contents of which are incorporated herein by reference in their entirety. Head 118 may have longitudinal slots (not shown) which may permit staples to pass through stapler cartridge 126 and pierce an intended target, e.g., tissue. In some embodiments, an actuation mechanism may be arranged to move proximally in a longitudinal direction from a distal end of stapler cartridge 126 toward a proximal end of cartridge 128 when actuated, contacting staples within stapler cartridge 126 and activating the staples through longitudinal slots, or a surface of the stapler cartridge, in order to couple staples to target tissue. Alternatively, in some embodiments, the actuation mechanism may be arranged to move distally in a longitudinal direction from a proximal end of stapler cartridge 126 toward a distal end of stapler cartridge 126 when actuated. In either manner, actuation mechanism may be actuated via the second drive mechanism, as discussed above. For example, actuation of a second inner wire in actuator 104, via a controller, may deploy staples into target tissue. In some examples, a single staple may extend through each slot. Each staple may be partially within the slot prior to deployment to assist with alignment of the staple with the slot. In some embodiments, two (or more) actuation mechanisms (not shown) may be required to actuate two (or more) different longitudinal rows of staples in stapler cartridge 126.

In some embodiments, head 118, including stapler cartridge 126, may be comprised of any appropriate biocompatible material, including flexible materials that may permit head 118 to flex laterally during insertion into, or positioning within, the body of the subject. Such flexibility may further permit stapler 114 to be carefully navigated through tortuous anatomy without causing trauma to surrounding tissue.

Anvil 116 may include a groove (not shown) positioned longitudinally that may align with the longitudinal slots of head 118, when stapler 114 is in a closed position (see FIG. 3). Once head 118 is actuated to deploy a staple and the legs of a deployed staple pierce through an intended target, the groove may act as a receiving base that effectively anvils the legs of a staple, as stapler 114 is being closed, so that the deployed staple is securely fastened to target tissue.

Referring to FIGS. 2-4, an example of a method of stapling an intended target, e.g., tissue, using the embodiment of a stapling mechanism illustrated in FIGS. 2-4 is further discussed below. A user may couple or attach stapling mechanism 100 to a medical device, e.g., endoscope 10, and deliver mechanism 100 and endoscope 10 into the body of a subject, e.g., via a natural orifice (such as a mouth or anus) and through a tortuous natural body lumen of the subject, such as an esophagus, stomach, colon, etc. A user may direct mechanism 100 and endoscope 10 to an intended target site by various means, including imaging. Once a target site is reached, a user may open stapler 114, if it is closed, by operation of a controller (not shown), which triggers wire 124 to pivot anvil 116 about stapler pivot 120. A user may then rotate stapler 114 in a clockwise or counter-clockwise direction by operation of the same or a different controller (not shown) that is attached to actuator 104, which may be moved longitudinally in either direction via the controller. It is noted that a user may also choose to rotate stapler 114 first, and then open stapler 114 after rotation thereof. The order of the stapler rotation and opening steps may be reversed and is not limited to a particular order. After positioning stapler 114 by rotating it, a user may manually maneuver the stapler or employ a mechanical means (not shown), including, but not limited to a grasper, suction, etc., that assists in placing the intended target, e.g., tissue, within the stapler, so that the intended target is positioned between head 118 and anvil 116 of stapler 114. A user may then staple the intended target by operating the same or a different controller, which triggers another drive mechanism, such as a wire, to actuate the deployment of a staple from stapler cartridge 126. Actuation of the controller may simultaneously deploy a staple and close the stapler, thereby stapling an intended target. The various mechanisms of stapling mechanism 100, including, but not limited to, rotation of stapler 114, opening/closing of stapler 114, and the deployment of staples from stapler cartridge 126, may be actuated by operation of the same controller, or different controllers.

It will be apparent to those skilled in the art that various modifications and variations can be made to the disclosed stapling mechanism without departing from the scope of the disclosure. For examples, the configuration of a coupler, actuator, and a stapler may be altered to suit any medical device, and are not limited to the examples described herein. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A fastening mechanism comprising:
- an actuator;
- a fastening device attached to a distal end of the actuator;
- a sheath; and
- a device coupler, wherein the device coupler includes a proximal support joined to a distal support by a coupler arm, wherein the coupler arm includes a curved surface configured to accommodate a shape of a medical device resting upon the coupler arm, wherein the fastening device is pivotably attached to the distal support, wherein the device coupler includes a proximal support fixed to a distal support, wherein the proximal support is fixed to the sheath, wherein the proximal support comprises at least one flexible arm, wherein the sheath covers a portion of the actuator and is fixedly coupled to the proximal support.

2. The fastening mechanism according to claim 1, wherein the actuator moves longitudinally to pivot the fastening device relative to the device coupler.

3. The fastening mechanism according to claim 1, wherein the actuator is longitudinally movable relative to the sheath.

4. The fastening mechanism according to claim 1, wherein the actuator includes at least one inner drive mechanism that actuates the fastening device to one or both of (1) open and close the fastening device and (2) deploy fasteners.

5. The fastening mechanism according to claim 1, wherein the fastening device is a stapler that includes a head and an anvil, and the head includes a stapler cartridge from which staples are held and deployed.

6. The fastening mechanism according to claim 5, wherein the stapler cartridge includes a plurality of longitudinal slots from which a plurality of staples are deployed.

7. The fastening mechanism according to claim 5, wherein the head is comprised of a flexible material that allows the head to flex laterally.

8. The fastening mechanism according to claim 1, wherein a proximal end of the actuator is connected to a controller that operates the fastening mechanism.

9. The fastening mechanism according to claim 8, wherein the controller operates at least one of (1) longitudinally moving the actuator in either direction, (2) opening the fastening device, and (3) simultaneously deploying fasteners and closing the fastening device.

10. The fastening mechanism according to claim 1, wherein the actuator is comprised of a flexible material.

11. The fastening mechanism according to claim 1, wherein the distal support defines a lumen with an open distal end or a clear barrier at an end of the lumen.

12. The fastening mechanism according to claim 1, wherein the device coupler removably attaches the fastening device to an outer surface of a distal end of a medical device.

13. A fastening mechanism comprising:
- an actuator;
- a stapler attached to a distal end of the actuator;
- a sheath covering a portion of the actuator and in which the actuator moves longitudinally relative to the sheath; and
- a device coupler for attaching the stapler to an outer surface of a distal end of a medical device;
- wherein the device coupler includes a proximal support fixed to a distal support by a coupler arm, wherein the proximal support is fixedly coupled to the sheath and comprises at least one flexible arm, wherein the coupler arm includes a curved surface configured to accommodate a shape of a medical device resting upon the coupler arm, and wherein the stapler is pivotably attached to the distal support of the device coupler, such that the stapler is pivotable with respect to the distal end of the medical device.

14. The fastening mechanism according to claim 13, wherein the medical device is an endoscope, and the proximal support and the distal support are fixed to a distal end of the endoscope.

15. The fastening mechanism according to claim 13, wherein the actuator is longitudinally movable relative to the sheath to pivot the stapler relative to the device coupler.

16. The fastening mechanism according to claim 13, wherein the actuator includes at least one inner drive mechanism that actuates the stapler to one or both of (1) open and close the stapler and (2) deploy staples.

17. A fastening mechanism comprising:
- a sheath, wherein an actuator extends through the sheath such that the sheath covers a portion of the actuator, and wherein the actuator is longitudinally movable relative to the sheath;
- a fastening device attached to a distal end of the actuator; and
- a device coupler including a proximal support fixed to a distal support by a coupler arm extending from the proximal support to the distal support, wherein the coupler arm includes a curved surface configured to accommodate a shape of a medical device resting upon the coupler arm, wherein the proximal support is fixedly coupled to the distal support and the sheath, wherein the proximal support comprises at least one flexible arm, and wherein the fastening device is pivotably attached to the distal support by a pivot pin that extends through a portion of the distal support and a portion of the fastening device.

18. The fastening mechanism according to claim 17, wherein the actuator moves longitudinally to pivot the fastening device relative to the device coupler.

19. The fastening mechanism according to claim 17, wherein the actuator includes at least one inner drive mechanism that actuates the fastening device to one or both of (1) open and close the fastening device and (2) deploy fasteners.

20. The fastening mechanism according to claim 17, wherein the fastening device is a stapler that includes a head and an anvil, and the head includes a stapler cartridge from which staples are held and deployed.

* * * * *